United States Patent [19]

Usami et al.

[11] 4,360,022
[45] Nov. 23, 1982

[54] SANITARY NAPKIN

[75] Inventors: Akira Usami, Sakai; Motoharu Kotani, Kawachinagano; Tomoko Goda, Kochi, all of Japan

[73] Assignees: Daisel Kagaku Kogyo Kabushikikaisha, Osaka; Fuji Eizai Kabushikikaisha, Kochi, both of Japan

[21] Appl. No.: 221,669

[22] Filed: Dec. 31, 1980

[30] Foreign Application Priority Data

Jan. 17, 1980 [JP] Japan .............................. 55-3094[U]

[51] Int. Cl.³ .............................................. A61F 13/16
[52] U.S. Cl. ................................................. 128/290 R
[58] Field of Search ................... 128/284, 287, 290 R, 128/296

[56] References Cited

U.S. PATENT DOCUMENTS

| 3,987,792 | 10/1976 | Hernandez et al. | 128/287 |
| 4,055,180 | 10/1977 | Karami | 128/287 |
| 4,055,184 | 10/1977 | Karami | 128/287 |
| 4,102,340 | 7/1978 | Mesek et al. | 128/287 |
| 4,184,902 | 1/1980 | Karami | 128/287 |
| 4,216,772 | 8/1980 | Tsuchiya et al. | 128/284 |
| 4,269,188 | 5/1981 | Nishizawa et al. | 128/287 |

Primary Examiner—C. Fred Rosenbaum
Attorney, Agent, or Firm—Jordan and Hamburg

[57] ABSTRACT

A sanitary napkin comprising a filler including a water-permeable layer of hydrophobic fibers for passing the body fluid therethrough and an absorbing layer underlying the layer for absorbing the fluid, and a water-permeable covering which covers the filler. The napkin is used with the water-permeable layer in contact with the human body. The water permeable layer has outstanding water permeability and functions to prevent reverse flow, permitting the absorbing layer to readily absorb the body fluid while preventing the fluid from returning toward the body. The napkin therefore has an agreeable feel at all times during use without feeling wet or sticky. The cushioning property of the water-permeable layer also gives a comfortable feel.

16 Claims, 5 Drawing Figures

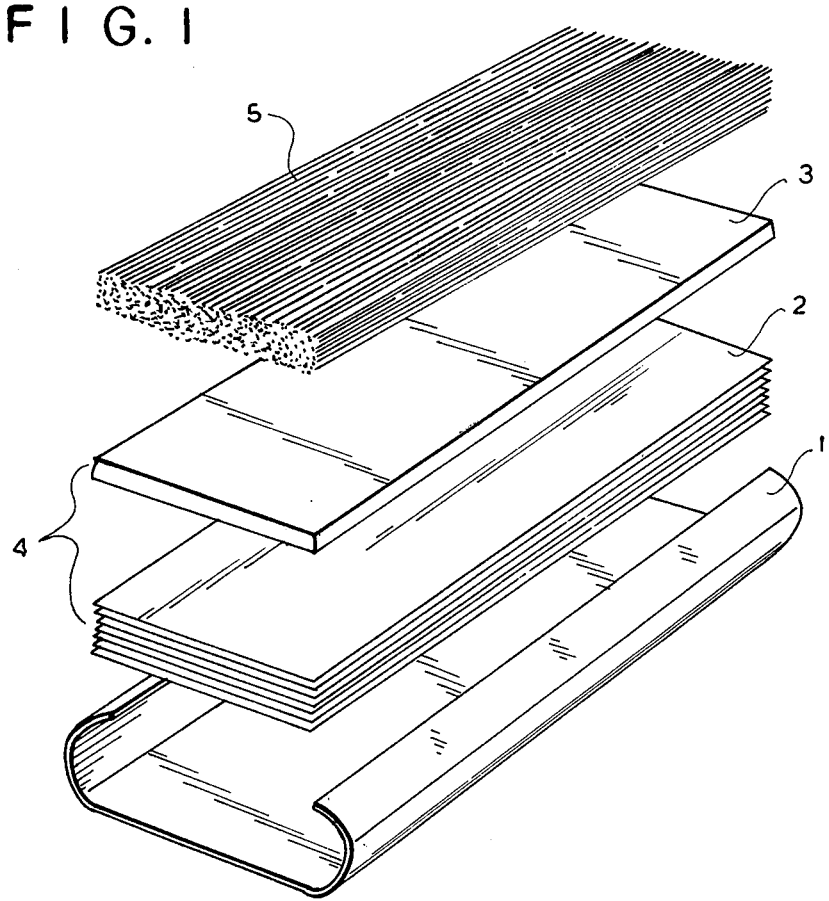
F I G. 1
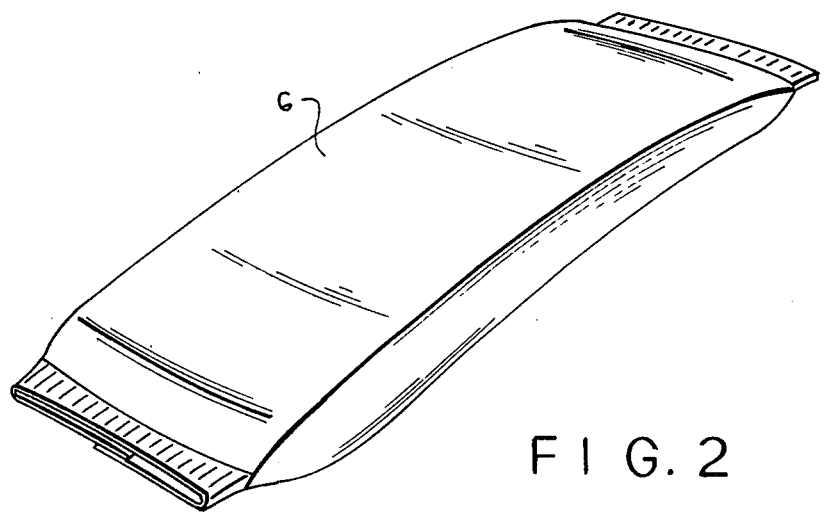
F I G. 2

SANITARY NAPKIN

The present invention relates to sanitary napkins.

Conventional sanitary napkins comprise an absorbing layer serving as the uppermost layer to be held in contact with the human body and made of a hydrophilic absorbent material, such as absorbent paper, absorbent cotton, pulverized pulp or the like, so that when having absorbed therein a large quantity of the body fluid, the napkin becomes sticky on its surface. Furthermore, when the absorbing layer is subjected to pressure, the body fluid once absorbed therein is likely to ooze or flow out reversely toward the body, consequently making the surface sticky. Thus the napkin becomes very uncomfortable to use and unsanitary.

Further since the body fluid is discharged in large quantities within a relatively short period of time in the initial stage of menstruation, the absorbing layer is unable to fully absorb the discharge in some cases, permitting the body fluid to remain on the surface of the absorbing layer and leak sideways when the layer is subjected to varying body pressures.

An object of the present invention, which has been accomplished to overcome the above drawbacks of conventional napkins, is to provide a sanitary napkin which is capable of readily absorbing the body fluid by an absorbing layer and preventing return of the fluid and which is therefore comfortable to use without feeling wet or sticky.

Another object of the invention is to provide a sanitary napkin which has outstanding ability to absorb the body fluid as diffused through its absorbent layer and which is therefore capable of efficiently absorbing and retaining the body fluid over the entire area of the absorbing layer.

Still another object of the invention is to provide a sanitary napkin comprising an absorbing layer which itself has high ability to absorb and retain the body fluid.

Other objects and advantages of the invention will become apparent from the following description of embodiments with reference to the accompanying drawings, in which:

FIG. 1 is an exploded perspective view showing a filler according to a first embodiment of the invention;

FIG. 2 is a perspective view showing the embodiment in its entirety;

Figure 3:
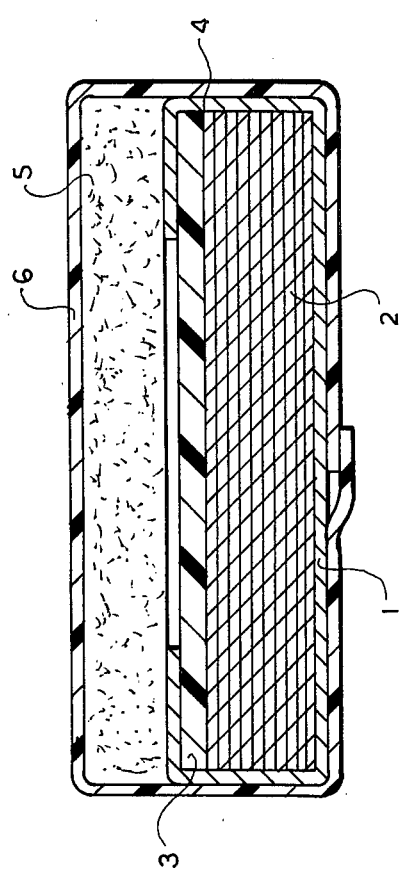
FIG. 3 is a view in cross section showing the same.

With reference to the first embodiment shown in FIGS. 1 to 3, a waterproof layer 1 is made of waterproof paper, such as a polyethylene sheet, laminated polyethylene paper, or the like. Indicated at 2 are sheets of auxiliary absorbent made of absorbent paper, such as crepe paper, paper-like cotton or the like. Placed over these sheets is an absorbent sheet 3 made from a highly water-absorbent high-molecular-weight polymer. Thus an absorbing layer 4 comprises the auxiliary absorbent 2 and the absorbent sheet 3. The absorbing layer 4 is placed over the waterproof layer 1, and the opposite side portions of the layer 1 are folded upward over the side portions of the absorbing layer 4 to laterally wrap the layer 4 with the layer 1, with a major portion of the upper surface of the absorbing layer 4 left exposed. A water-permeable layer 5 is then placed over the absorbing layer 4. The whole assembly is enclosed with a covering 6 which is highly permeable to water. The covering 6 is sealed at its longitudinally opposite ends. Thus a sanitary napkin of this invention is completed.

The covering 6 is made of a material which has high water-permeability and feels comfortable. Examples of materials which have an especially good feel are those made predominantly of a nonwoven fabric, such as polyesterblended nonwoven fabric, rayon nonwoven fabric, rayon paper laminated with cotton nonwoven fabric, etc. Rayon paper, Japanese paper and like papers are also usable.

Examples of highly water-absorbent high-molecular-weight polymers useful for the absorbent sheet 3 are starch derivatives (graft copolymers of starch with acrylonitrile, acrylamide, acrylic acid, acrylate, methacrylonitrile, methacrylate, etc., partially hydrolyzed products of such copolymers, or cross-linked products thereof), cross-linked carboxymethylcellulose, polyvinyl alcohol, sodium polyacrylate, etc. These polymers have very high permeability to water, swell to a gel on absorption of water, and possess much higher water retentivity than usual absorbent papers and pulverized pulps. Typical of absorbents made of such substance is a special absorbent paper (trade mark, "GSP SHEET,") product of Japan Vilene, Co., Ltd. This sheet is produced by feeding cotton-like pulp fully loosened by a hammer mill and a powder of alkali metal salt (GSP) of partially hydrolyzed product of starch-polyacrylonitrile graft copolymer in a specified weight ratio to a mixer as entrained in an air stream, stirring the pulp and powder to obtain a uniform mixture, passing the mixture through a distributor to form a web weighing $70 \pm 12$ g/m$^2$, and pressing the web into a sheet with application of heat and moisture. The sheet has especially high ability to absorb water among other absorbents prepared from highly water-absorbent high-molecular-weight polymers. In fact, the sheet is capable of absorbing water in an amount of as much as 30 times the weight thereof.

The water-permeable layer 5 is prepared from tows of hydrophobic fibers, such as cellulose acetate, polypropylene, polyester or like fibers, by opening the tows into strip-like bundles of long fibers and arranging the bundles in parallel along the length of the napkin. The bundles of long fibers may be joined together with a water-permeable binder. Alternatively the water-permeable layer 5 of the illustrated form can be prepared by arranging short hydrophobic fibers lengthwise to obtain assemblies resembling long fibers, and arranging the assemblies in parallel in the form of a strip.

The water-permeable layer 5 thus composed of a group of cellulose acetate or like hydrophobic fibers is highly permeable to water because of the properties of the material, readily permits penetration of water and thereafter prevents reverse flow of the water. The layer 5 comprising the group of oriented long fibers has the characteristic that water is diffused preferentially lengthwise of the fibers, i.e. longitudinally of the napkin, by the capillarity of the fibers, so that the layer in its entirety permits water to pass therethrough while spreading in an elliptical form. Since the material of the water-permeable layer has high elasticity against external pressure, the layer 5 has a high cushioning property and a comfortable feel. Especially when the hydrophobic fibers used are cellulose acetate fibers which are up to 8 denier in the fineness of single fiber and 35000 to 50000 denier in overall fineness, the water-permeable layer is highly compressible and has a greatly improved cushioning property. Also usable as such fibers are cellulose acetate fibers recovered from cigarette filter plugs.

The sanitary napkin of the foregoing construction is used with the water-permeable layer 6 in contact with the human body. During use, the body fluid discharged passes through the covering 6 and the layer 5 and is absorbed by the absorbing layer 4. Since the water once absorbed by the layer 4 is prevented by the water-permeable layer 5 from flowing reversely toward the body, the surface of the napkin in contact with the body does not feel wet but has a comfortable feel at all times and is sanitary. According to the present embodiment, the water-permeable layer 5 comprises hydrophobic fibers which are arranged along the length of the napkin and which therefore have an effective capillary action, spreading water longitudinally of the absorbent and causing the fluid to pass through the layer 5 in an elliptical form. Thus the layer 5 diffuses the fluid with greatly improved efficiency, enabling the absorbing layer to absorb a greatly increased amount of fluid, whereas conventional napkins absorb the fluid only over a limited circular area although the napkins are rectangular. Moreover the cushioning action of the fibers affords a comfortable feel.

The absorbent sheet 3 of the absorbing layer 4 for absorbing the body fluid passing through the layer 5 is made from a highly water-absorbent high-molecular-weight polymer as already described and therefore has very high ability to absorb water, that is, the body fluid. Since the sheet 3 swells and forms a gel upon absorption of water, the sheet is free of the drawback heretofore experienced with usual absorbents, such as crepe paper, absorbent paper and absorbent cotton. With such conventional absorbents, the body fluid once absorbed remains liquid to saturate the absorbent, possibly overflowing the napkin through a break in the covering. In other words, the absorbent sheet 3 has high ability to retain the body fluid absorbed therein.

Because the absorbent sheet 3 has such outstanding ability to absorb and retain water, the absorbing layer 4 achieves a satisfactory result even when comprising one to several absorbent sheets 3 only. The auxiliary absorbent 2 beneath the sheet 3 assures safety in the presence of an abnormally large amount of body fluid. Accordingly the body fluid is absorbed and retained usually by the absorbent sheet 3 only, and the fluid absorbed by the auxiliary absorbent is little, if any. The auxiliary absorbent 2 need not always be provided, therefore. Should the body fluid pass through the absorbing layer 4, there is no likelihood of leakage since the waterproof layer 1 is provided.

Given below are experimental examples in which the sanitary napkins described above were tested for water absorption and water retentivity.

Experimental Example 1

Specimens of the napkin shown in FIGS. 1 to 3 were tested for water absorption. The specimen weighs 5 g and is made up of the components listed in Table 1. The double-faced adhesive tape shown in Table 1 was attached to the bottom side of the napkin for holding the napkin in place.

TABLE 1

| Component | wt. % |
| --- | --- |
| Water-permeable layer | 20.0 |

TABLE 1-continued

| Component | wt. % |
| --- | --- |
| (cellulose acetate fibers) | |
| Absorbent sheet | 16.0 |
| (GSP SHEET) | |
| Auxiliary absorbent | 41.4 |
| (8 sheets of absorbent paper) | |
| Waterproof layer | 9.6 |
| (polyethylene film laminate paper) | |
| Covering | 11.6 |
| (polyester/rayon blended nonwoven fabric) | |
| Double-faced adhesive tape | 1.4 |

The water absorption test was conducted based on Standards for Sanitary Goods (Notification No. 285 of the Ministry of Health and Welfare, Japanese Government, May 24, 1966), Standard III and according to the test method specified by the Japanese Pharmacopoeia (Notification No. 73 of the same, April 1971). The test method is as follows.

The specimen is placed, with the water-permeable layer up, on a 10-mesh (1680μ) metal net of known weight. Water is then gently poured with a beaker onto the specimen over the entire surface thereof to cause the whole specimen to completely absorb water. Water is continuously poured until the water overflows the specimen. The specimen is then allowed to stand for 1 minute and thereafter weighed. The amount of water absorbed is the weight of the specimen after the application of water minus the weight of the specimen before the application. The amount of water is listed also in terms of "times" based on the initial weight of the specimen.

Table 2 shows the results.

TABLE 2

| Specimen No. | Weight of specimen (g) | Amount of water absorbed (g) | Times |
| --- | --- | --- | --- |
| 1 | 5.0 | 127.15 | 25.43 |
| 2 | 5.0 | 128.1 | 25.62 |
| 3 | 5.0 | 126.6 | 25.32 |
| 4 | 5.0 | 128.8 | 25.76 |
| 5 | 5.0 | 128.4 | 25.68 |
| Average | 5.0 | 127.81 | 25.56 |

Experimental Example 2

The same specimens as used above were prepared except that the water-permeable layer 5 and the absorbent sheet 3 were replaced by absorbent paper approximately equivalent thereto in weight. The specimens were tested for water absorption in the same manner as above. The results are given in Table 3.

TABLE 3

| Specimen No. | Weight of specimen (g) | Amount of water absorbed (g) | Times |
| --- | --- | --- | --- |
| 6 | 5.1 | 80.7 | 15.82 |
| 7 | 5.05 | 83.9 | 16.61 |
| 8 | 5.1 | 89.3 | 17.51 |
| 9 | 5.15 | 87.7 | 17.02 |
| 10 | 5.05 | 82.9 | 16.42 |
| Average | 5.09 | 84.9 | 16.68 |

Experimental Examples 1 and 2 show that the specimens No. 1 to No. 5 according to the invention are all acceptable in the light of the Standard for Sanitary Goods and absorb much larger amounts of water than the blank specimens No. 6 to No. 10 in which the absorbing layer is made only of absorbent paper.

Experimental Example 3

Specimens No. 11 to No. 15 were prepared from the same components as listed in Table 1 and were tested for water retentivity. The test was conducted by the following method.

In the bottom of a container made of thin iron sheet and having inside dimensions of 165 mm in length, 67 mm in width and 50 mm in depth is fitted a 3-mm-thick apertured iron plate formed with 27 circular apertures 6 mm in diameter. The specimen is placed into the container, and a thin iron plate conforming to the size of the container is further placed on the specimen. The container is then immersed for 5 minutes in purified water adjusted to 25° C.±2° C. Subsequently the specimen is gently withdrawn from the water along with the container, allowed to stand for 2 minutes, and further allowed to stand for 1 minute with a weight (weighing 5436 g and having a bottom area of 165 mm×67 mm) gently placed thereon. Thus the specimen is subjected to a load of about 50 g/cm². The weight is thereafter removed, and drops of water are gently wiped off the specimen and the container, which are then weighed to obtain a weight B. The amount of water retained in the specimen, X, is the weight B minus the weight C of the container (including the apertured iron plate and the thin iron plate) and the weight of the specimen, A.

$X = B-C-A$

Water retentivity = $X/A$
Table 4 shows the results.

TABLE 4

| Specimen No. | Weight of specimen (g) | Amount of water retained (g) | Water retentivity |
|---|---|---|---|
| 11 | 5.0 | 70.8 | 14.17 |
| 12 | 5.0 | 76.0 | 15.21 |
| 13 | 5.0 | 68.7 | 13.75 |
| 14 | 5.0 | 71.9 | 14.38 |
| 15 | 5.0 | 70.8 | 14.17 |
| Average | 5.0 | 71.6 | 14.33 |

Experimental Example 4

Blank specimens were prepared from the same components as listed in Table 1 except that the water-permeable layer 5 and the absorbent sheet 3 were replaced by absorbent paper approximately equivalent thereto in weight. The specimens were tested for water retentivity in the same manner as in Experimental Example 3. Table 5 shows the results.

TABLE 5

| Specimen No. | Weight of specimen (g) | Amount of water retained (g) | Water retentivity |
|---|---|---|---|
| 16 | 5.0 | 38.5 | 7.7 |
| 17 | 5.1 | 40.5 | 7.94 |
| 18 | 5.1 | 36.5 | 7.16 |
| 19 | 5.05 | 38.5 | 7.62 |
| 20 | 5.0 | 39.3 | 7.86 |
| Average | 5.05 | 38.66 | 7.66 |

Experimental Examples 3 and 4 reveal that the specimens No. 11 to No. 15 according to the invention retain much larger amounts of water than the blank specimens No. 16 to No. 20 in which the absorbing layer is made only of absorbent paper.

Figure 5:
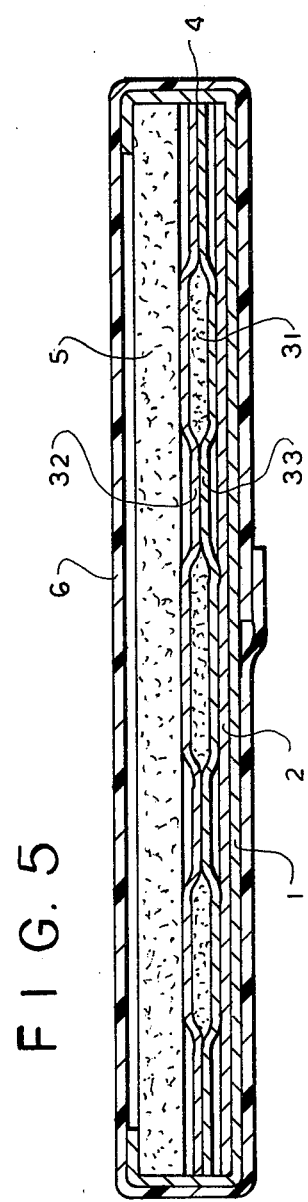
FIG. 5 is an enlarged view in cross section showing the second embodiment.
Figure 4:
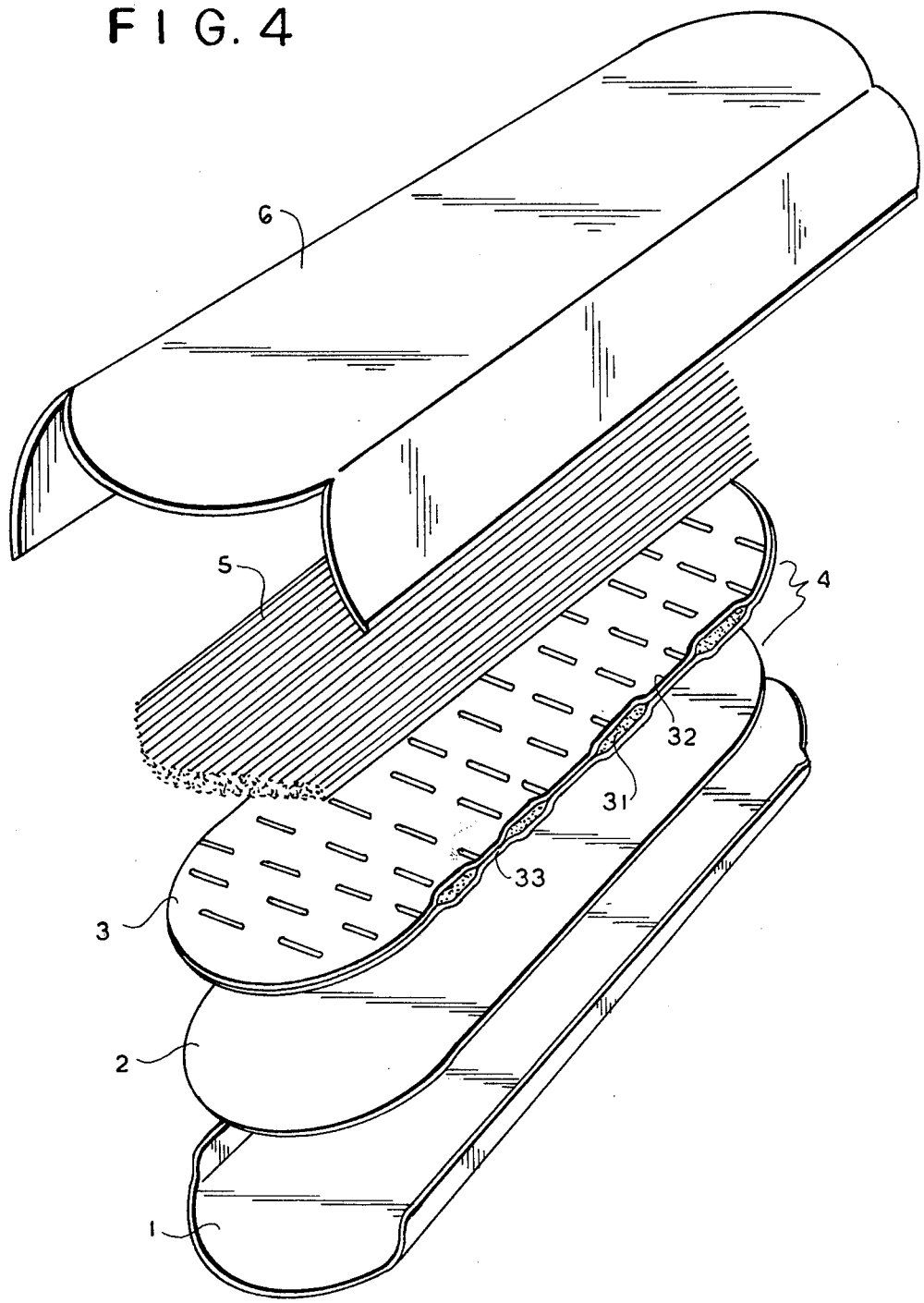
FIG. 4 is an exploded over-all perspective view showing a second embodiment of the invention.

With reference to FIGS. 4 and 5, a second embodiment of the invention will be described.

The second embodiment includes an absorbing layer 4 consisting essentially of an absorbent sheet 3, which is prepared by sandwiching a mixture 31 of pulverized pulp and a powder of highly water-absorbent high-molecular-weight polymer between sheets 32 and 33 of absorbent paper, such as tissue paper, which is thin, soft and tough, and partially embossing the assembly to obtain a thin sheet. An auxiliary absorbent 2, which is a sheet of absorbent paper in the illustrated embodiment, may comprise a plurality of such sheets when so desired, as is the case with the first embodiment. The second embodiment has the same construction as the first with the exception of the above features.

Highly water-absorbent high-molecular-weight polymers useful for the mixture 31 are those already exemplified for the first embodiment. Especially the mixture of pulverized pulp and alkali metal salt (GSP) of partially hydrolyzed product of starch-polyacrylonitrile graft copolymer for preparing GSP SHEET is suitable for use as the mixture 31. When such a mixture is sandwiched between the sheets 32, 33 of absorbent paper, such as tissue paper, and the assembly is made into a sheet, the absorbent sheet 3 has an agreeable soft hand and a very good feel without feeling stiff or rough. The high water absorbing and retaining properties of the mixture of polymeric powder and pulverized pulp, and the water-absorbing ability of the absorbent paper sheets 32, 32 combine to give greatly improved ability to absorb water. The assembly is embossed partially but uniformly over the entire sheet 3 as illustrated, whereby the mixture 31 can be held between the sheets of paper 32, 32 against displacement with uniform distribution over the entire area. The embossing process compresses the assembly to a thin sheet in its entirety while enabling the sheet to retain its shape effectively.

While the second embodiment has outstanding water absorbing and retaining properties characteristic of the absorbent sheet 3 as afforded by GSP SHEET in the first embodiment, the second embodiment has another advantage that the mixture, even when swelling to a gel, is held between the absorbent paper sheets 32, 33 without separating into loose fragments, enabling the absorbent sheet 3 retain its shape during use. Additionally the mixture 31 can be thoroughly impregnated with water through the sheets of paper 32, 33, thus permitting the sheet 3 to fully exhibit its absorbing and retaining ability. These are outstanding advantages of the second embodiment.

The water-permeable layer is prepared, for example, by opening long crimped cellulose acetate fibers and arranging the fibers along the length of the napkin to be produced. Such cellulose acetate long fibers crimped and opened have high elasticity and afford a good cushioning property and therefore give an enhanced comfortable feel to the product. The crimp serves to spread the body fluid longitudinally of the napkin and also lead the fluid in the direction of its thickness in a well-balanced manner. Useful acetate long fibers may be circular, I-shaped, Y-shaped, C-shaped or otherwise shaped in cross section. Fibers of such irregular cross section are bulkier than those of circular cross section, affording a better cushioning property.

The sanitary napkin of this invention, which comprises a water-permeable layer of hydrophobic fibers and an absorbing layer underlying the former, readily absorbs the body fluid without permitting return of the fluid toward the body, is therefore clean and comfortable during use without feeling wet or sticky, and has a soft feel and a good cushioning property.

Because the water-permeable layer is prepared by opening tows of hydrophobic fibers into strip-like bundles of long fibers and arranging the bundles in parallel to the length of the napkin, water can be diffused longitudinally of the napkin and led through the layer in an elliptical form when the layer is seen in its entirety. As compared with conventional napkins which absorb the body fluid only over a limited circular area although the napkins are rectangular, the napkin of this invention diffuses the fluid more efficiently and absorbs the fluid in greatly increased amount in its entirety.

The napkin has remarkably enhanced ability to absorb and retain the body fluid when the absorbing layer consists partly or entirely of an absorbent sheet made from a highly water-absorbent high-molecular-weight polymer. When so made, the absorbing layer is available with an exceedingly smaller thickness than is heretofore possible, is more comfortable to use and is advantageous for packaging and transport.

Further according to the invention, an absorbent sheet is prepared from a mixture of highly water-absorbent high-molecular weight polymer and pulverized pulp, by sandwiching the mixture between sheets of tough and thin absorbent paper, such as tissue paper, and embossing the resulting assembly to obtain a sheet, which no longer feels stiff or rough but has a soft and agreeable feel.

Thus the napkin of this invention has various advantages for use.

What is claimed is:

1. A sanitary napkin comprising an elongated filler which in turn comprises a water-permeable layer formed of hydrophobic fibers and an absorbing layer underlying said water-permeable layer, and a water-permeable covering which covers said filler, said water-permeable layer of hydrophobic fiber comprising rows of hydrophobic fibers arranged in strip-like bundles of elongated fibers disposed generally parallel to the length of said sanitary napkin, whereby the fluid diffuses along the fibers a greater amount in a longitudinal direction as compared to a transverse direction such that the fluid diffuses along the napkin by the capillarity of the fibers to spread in a generally elliptical form.

2. A sanitary napkin according to claim 1 wherein said absorbing layer comprises an absorbent sheet prepared from a highly water-absorbent, high-molecular-weight polymer and an auxiliary absorbent sheet underlying said absorbent sheet.

3. A sanitary napkin according to any one of claim 1 wherein said filler further comprises a waterproof layer formed on the underside of said absorbing layer.

4. A sanitary napkin according to claim 2 wherein said absorbent sheet comprises a mixture of said highly water-absorbent, high-molecular-weight polymer and pulverized pulp, wherein said mixture is formed into a web and the web is shaped into a sheet.

5. A sanitary napkin according to claim 2 wherein said absorbent sheet comprises a mixture of said highly water-absorbent, high-molecular-weight polymer and pulverized pulp, sheets of thin and tough absorbent paper between which said mixture is sandwiched, the resultant assembly being partially embossed to obtain an integral sheet.

6. A sanitary napkin according to claim 1, wherein said fibers of said water-permeable layer are opened-up, elongated crimped fibers having high elasticity and good cushioning properties.

7. A sanitary napkin according to claim 1, wherein said fibers of said water-permeable layer have an irregular cross section.

8. A sanitary napkin according to claim 7, wherein said irregular cross section is I-shaped.

9. A sanitary napkin according to claim 7, wherein said irregular cross section is Y-shaped.

10. A sanitary napkin according to claim 7, wherein said reeigular cross section is C-shaped.

11. A sanitary napking according to claim 1, wherein said irregular cross section is constructed and arranged to provide bulky fibers affording enhanced cushioning properties.

12. A sanitary napkin according to claim 1 wherein said water-permeable layer is made of a material selected from cellulose acetate, polypropylene, and polyester.

13. A sanitary napkin according to claim 1 further comprising a binder joining together said hydrophobic fibers of said water-permeable layer.

14. A sanitary napkin according to claim 1 wherein said water-permeable layer is constructed to readily permit penetration of fluid and thereafter to prevent reverse flow of said fluid.

15. A sanitary napkin according to claim 1 wherein said absorbent sheet is constructed to swell and form a gel upon absorption of liquid.

16. A sanitary napkin comprising an elongated filler which in turn comprises a water-permeable layer formed of hydrophobic fibers and an absorbing layer underlying said water-permeable layer, and a water-permeable covering which covers said filler, said water-permeable layer of hydrophobic fibers comprising short hydrophobic fibers arranged lengthwise to obtain assemblies resembling elongated fibers in which said assemblies are disposed parallel to the length of the sanitary napkin, whereby the fluid diffuses along the fibers a greater amount in a longitudinal direction as compared to a transverse direction such that the fluid diffuses along the napkin by the capillarity of the fibers to spread in a generally elliptical form.

* * * * *